(12) United States Patent
Zhao et al.

(10) Patent No.: US 8,796,625 B2
(45) Date of Patent: Aug. 5, 2014

(54) CARBON NANOTUBE-HYDROGEN PEROXIDE HYBRID BASED OPTICAL SENSING METHOD FOR ASSESSMENT OF ANTIOXIDANT POTENCY

(75) Inventors: Wei Zhao, Little Rock, AR (US); Boshan Zhao, Little Rock, AR (US)

(73) Assignee: Board of Trustees of the University of Arkansas, Little Rock, AR (US)

( * ) Notice: Subject to any disclaimer, the term of this patent is extended or adjusted under 35 U.S.C. 154(b) by 896 days.

(21) Appl. No.: 12/754,040

(22) Filed: Apr. 5, 2010

(65) Prior Publication Data

US 2010/0328647 A1    Dec. 30, 2010

Related U.S. Application Data

(60) Provisional application No. 61/212,111, filed on Apr. 7, 2009.

(51) Int. Cl.
*G01J 5/00* (2006.01)

(52) U.S. Cl.
USPC ........................................ 250/338.1

(58) Field of Classification Search
USPC ........................................ 250/338.1
See application file for complete search history.

(56) References Cited

U.S. PATENT DOCUMENTS

| 2006/0040381 A1* | 2/2006 | Zhao et al. | 435/287.9 |
| 2007/0026388 A1* | 2/2007 | Doorn et al. | 435/5 |
| 2009/0123956 A1* | 5/2009 | Koliakos et al. | 435/25 |

OTHER PUBLICATIONS

Y. Xu, P. E. Pehrsson, L. Chen, W. Zhao, J. Am. Chem. Soc, 130(31) (2008) 10054-10055. Controllable Redox Reaction of Chemically Purified DNA-Single Walled Carbon Nanotube Hybrids with Hydrogen Peroxide.
L. Pauling, Vitamin C and the Common Cold, San Francisco, CA, W. H. Freeman and Company, 1970.
Collins, C. H.; Silva, C. R.; Simoni, J. A.; Volpe, P. L. O. J. Chem. Educ., 1999, 76, 1421-1422. Ascorbic acid as a Standard for Iodometric Titrations.
Paim, A. P.; Reis, B. F. Anal. Sci., 2000, 16, 487-491. An Automatic Spectrophotometric Titration Procedure for Ascorbic Acid Determination in Fruit Juices and Soft Drinks Based on Volumetric Fraction Variation.
A. Zafra-Gomez, A. Garballo, J. C. Morales, L. E. Garcia-Ayuso, J. Agric. Food Chem. 54 (2006) 4531-4536. Simultaneous Determination of Eight Water-Soluble Vitamins in Supplemented Foods by Liquid Chromatography.
A. M. Maia, A. R. Baby, W. J. Yasaka, E. Suenaga, T. M. Kaneko, M. V. R. Velasco, Talanta 71 (2007) 639-643. Validation of HPLC Stability-indicating Method for Vitamin C in Semisolid Pharmaceutical/Cosmetic Preparations with Glutathione and Sodium Metabisulfite, as Antioxidants.

(Continued)

*Primary Examiner* — David Porta
*Assistant Examiner* — Edwin Gunberg
(74) *Attorney, Agent, or Firm* — Morris, Manning & Martin, LLP; Tim Tingkang Xia, Esq.

(57) ABSTRACT

An ultrasensitive dual optical method for measuring antioxidant concentration and total antioxidant capacity is provided. Using the process, the detection limit for vitamin C is as low as 7 nM. The method is based on a hybrid of single walled carbon nanotubes (SWNT) with hydrogen-peroxide. The method provides is a robust, cheap, fast, and reusable optical sensing method for antioxidant and total antioxidant capacity measurement in foods and plasma. The method can also be developed as a miniature assay for both in vitro and in vivo detection.

25 Claims, 10 Drawing Sheets

(56) References Cited

OTHER PUBLICATIONS

Lagier, C. M.; Verdini, R. A. J. Agric. Food Chem., 2000, 48, 2812-2817. Voltammetric Iodometric Titration of Ascorbic Acid with Dead-Stop End-Point Detection in Fresh Vegetables and Fruit Samples.

T. Rohani, M. A. Taher, Talanta 78 (2009) 743-747. A New Method for Electrocatalytic Oxidation of Ascorbic Acid at the Cu(II) Zeolite-Modified Electrode.

X. Wu, L. Gu, J. Holden, D. B. Haytowitz, S. E. Gebhardt, G. Beecher, R. L. Prior, J. Food Compo. Anal. 17 (2004) 407-422. Development of a Database for Total Antioxidant Capacity in Foods: A Preliminary Study.

D. Huang, B. Ou, R. L. Prior, J. Agric. Food Chem. 53 (2005) 1841-1856. The Chemistry behind Antioxidant Capacity Assays.

Ph. Avouris, Z. Chen, V. Perebeinos, Nature Nanotech. 2 (2007) 605-615. Carbon-Based Electronics.

L. Zhang, S. Zaric, X. Tu, W. Zhao, H. Dai, J. Am. Chem. Soc. 130(8) (2008) 2686-2691 Assessment of Chemically Separated Carbon Nanotubes for Nanoelectronics.

D.A. Tsyboulski, S. M. Bachilo, R. B. Weisman, Nano Lett. 5 (2005) 975-979. Versatile Visualization of Individual Single-Walled Carbon Nanotubes with Near-Infrared Fluorescence Microscopy.

P. Cherukuri, S. M. Bachilo, S. H. Litovsky, R. B. Weisman, J. Am. Chem. Soc. 126 (2004) 15638-15639. Near-Infrared Fluorescence Microscopy of Single-Walled Carbon Nanotubes in Phagocytic Cells.

W. Zhao, C. Song, P. E. Pehrsson, J. Am. Chem. Soc. 124 (2002) 12418-12419. Water-Soluble and Optically pH Sensitive Single-Walled Carbon Nanotubes from Surface Modification.

Z. Liu, C. Davis, W. Cai, L. He, X. Chen, H. Dai. PNAS 105 (2008) 1410-1415. Circulation and Long-Term Fate of Functionalized, Biocompatible Single-Walled Carbon Nanotubes in Mice Probed by Raman Spectroscopy.

X. Tu, P. E. Pehrsson, W. Zhao, J. Phys. Chem. C. 111 (2007) 17227-17231. Redox Reaction of DNA-Encased HiPco Carbon Nanotubes with Hydrogen Peroxide: A Near Infrared Optical Sensitivity and Kinetics Study.

Y. Xu, P. E. Pehrsson, L. Chen, R. Zhang, W. Zhao, J. Phys. Chem. C. 111 (2007) 8638-8643. Double Stranded DNA-Single Walled Carbon Nanotube Hybrids for Optical Hydrogen Peroxide and Glucose Sensing.

C. Song, P. E. Pehrsson, W. Zhao, J. Phys. Chem. B. 109 (2005) 21634-21639. Recoverable Solution Reaction of HiPco Carbon Nanotubes with Hydrogen Peroxide.

C. Song, P. E. Pehrsson, W. Zhao, J. Mater. Res. 21 (2006) 2817-2823. Optical Enzymatic Detection of Glucose Based on Hydrogen Peroxide-Sensitive HiPco Carbon Nanotubes.

Pisoschi et al., "Total Antioxidant Capacity of Some Commercial Fruit Juices: Electrochemical and Spectrophotometrical Approaches" Molecules, p. 480-493, Jan. 14, 2009.

* cited by examiner

CARBON NANOTUBE-HYDROGEN PEROXIDE HYBRID BASED OPTICAL SENSING METHOD FOR ASSESSMENT OF ANTIOXIDANT POTENCY

This application claims the benefit of Provisional U.S. Patent Application Ser. No. 61/212,111, filed on Apr. 7, 2009, which is incorporated by reference herein in its entirety.

The section headings used herein are for organizational purposes only and should not be construed as limiting the subject matter described herein in any way.

BACKGROUND

1. Field

This application relates generally to methods for detecting and, in particular, to methods for detecting the concentration and capacity of antioxidants in a sample.

2. Background of the Technology

Antioxidants such as vitamin C from fruits and vegetables provide a crucial protection capacity to fight free radicals which are implicated in the development of more than fifty diseases. Determination of antioxidant concentration in foods or other biological systems, including blood, is of great importance [1-7].

There are various methods for measuring vitamin C including conventional iodometric titration [2], spectrophotometric methods [3], chromatographic methods [4,5], and electrochemical methods [6,7]. These methods often involve several steps or multi chemical agents for concentration determination. They are time-consuming and the detection limit is usually at about μM levels or higher [4-7].

There is also great interest in determining total antioxidant capacity [8,9]. Representative methods include the oxygen radical absorbance capacity (ORAC) assay for antioxidant potency measurement [8,9]. The ORAC assay uses a fluorescent probe whose fluorescence decay is an indication of damage from its reaction with a free radical such as peroxyl radicals [8,9]. The inhibition of free radical damage by an antioxidant, as reflected in the protection against the fluorescence decay in the ORAC assay, is a measure of the antioxidant capacity of the antioxidant against the free radical [8,9]. However, there are certain drawbacks to using this method. First, the sample size required is usually relatively large, more than 1 gram for solids and >50 mL for liquids. In addition, the fluorescent probes emit visible light, a region where other biospecies may emit, thus causing interference. The probes may be subjected to photobleach, and they are damaged by free radicals and are therefore not reusable. The probes may not work with both hydrophilic and hydrophobic antioxidants so specific probes have to be designed for a particular application. In addition, the sensitivity is low and not suitable for in vivo applications.

Accordingly, there still exists a need for improved methods for antioxidant detection.

SUMMARY

A method is provided which comprises:
measuring a first absorbance value of a composition comprising single walled carbon nanotubes and $H_2O_2$ at one or more wavelengths in the near infra-red;
adding a sample to the composition;
subsequently measuring a second absorbance value of the composition at the one or more wavelengths; and
determining the difference between the first and second absorbance values;
wherein the difference between the first and second absorbance values is an indication of the antioxidant concentration or the antioxidant capacity of the sample.

A method is also provided which comprises:
(a) measuring a first absorbance value of a composition comprising single walled carbon nanotubes and $H_2O_2$ at one or more wavelengths in the near infra-red;
(b) adding a calibration sample comprising a known concentration of an antioxidant to the composition;
(c) subsequently measuring a second absorbance value of the composition at the one or more wavelengths;
(d) determining the difference between the first and second absorbance values;
(e) repeating steps (a)-(d) for one or more additional calibration samples having different known concentrations of the antioxidant; and
(f) determining the relationship between antioxidant concentration and the difference between the first and second absorbance values.

These and other features of the present teachings are set forth herein.

BRIEF DESCRIPTION OF THE DRAWINGS

The skilled artisan will understand that the drawings, described below, are for illustration purposes only. The drawings are not intended to limit the scope of the present teachings in any way.

FIGS. 2(a)-2(e) are schematics showing steps in the flowchart of FIG. 1, wherein FIGS. 2(a)-(d) correspond to steps (a)-(d), respectively, of the flowchart of FIG. 1 and wherein FIG. 2(e) shows the reaction cycle.

DESCRIPTION OF THE VARIOUS EMBODIMENTS

An ultrasensitive dual method for measuring antioxidants and total antioxidant capacity is provided. The detection limit for vitamin C is as low as 7 nM ($7 \times 10^{-9}$ M). The method is based on a hybrid of SWNT with hydrogen-peroxide. It is a robust, cheap, fast, and reusable optical sensing method for antioxidant and total antioxidant capacity measurement in foods and plasma. It can be developed as a miniature assay for in vitro and in vivo detection.

Antioxidants such as Vitamin C from fruits and vegetables provide a crucial protection capacity to fight free radicals which are implicated in the development of more than fifty diseases. Determination of antioxidant concentration in foods or other biological systems including blood is of great importance. Single-walled carbon nanotubes (SWNTs) emerge as a powerful material for electronic and optical sensing applications because of their unique nanoscale one-dimensional structure which is extremely sensitive to environment changes. Optical sensors based on SWNTs that can be used for antioxidant detection with high sensitivity are described herein.

Single-walled carbon nanotubes (SWNTs) have emerged as a powerful material for electronic and optical sensing applications because of their unique nanoscale one-dimensional structure which is extremely sensitive to environment changes [10-20]. For sensing applications, SWNTs offer several advantages: (1) their near infrared (NIR) features are in an important spectral window (800-1500 nm) that could be covered by the semiconducting laser wavelengths currently used in optical communications; (2) their spectra fall into the biologically transparent near-IR region of 800-1300 nm, making them attractive for in vivo biological optical detection applications; (3) they possess a high NIR fluorescence contrast, which may allow them to serve as a fluorophore in biochemically targeted tissue markers for selective detection and imaging; (4) they are highly photostable and do not photobleach; (5) they can be cleared from animal organs and excreted from the body, and are safe for animals [15] so SWNT-based labels are suitable for in vivo biological applications; (6) their nano-sized one-dimensional structure may allow them to be integrated into miniature devices with other nanosensors such as field effect transistor sensors; and (7) the same material SWNTs alone can also be used for free radical sensing with high sensitivity [16-20]. The SWNT-based optical sensing method can detect $H_2O_2$ as low as 8 µM [16]. Thus SWNTs and their hybrids may offer multifunctionalities for optical biosensing.

A highly sensitive optical sensing method for measuring antioxidants and total antioxidant capacity based on a single-walled carbon nanotube (SWNT)-hydrogen peroxide hybrid system is provided. In the system, SWNTs and hydrogen peroxide form a charge transfer complex accompanied with the suppression of SWNT characteristic near infrared spectral intensity which offers very low background interference. When antioxidant vitamin C is added, the complex reacts with it, with an instantaneous recovery of the suppressed spectral intensity. The amount of recovered spectral intensity is proportional to vitamin C concentration. The limit of detection can be as low as 7 nM.

When the hydrogen peroxide is in an excess amount, the remaining hydrogen peroxide continues reacting with SWNTs, so the vitamin C-recovered SWNT spectral intensity decreases again over time. If there are remaining antioxidants in the sample, then they also compete with SWNTs to react with the hydrogen peroxide. The decay rate of the spectral intensity and the area of the decay curve are each sensitive to the total antioxidant concentration in the sample and therefore provide a powerful means to compare the antioxidant capacity of foods or antioxidant concentration in biological systems including blood. The SWNT is structurally robust and the reaction is reversible, enabling the reuse of the hybrids. Furthermore, SWNTs' nano-sized one-dimensional structure may allow them to be integrated into miniature devices with other nanosensors such as field effect transistor sensors for multiplexing assays for in vitro and in vivo detection.

In the SWNT-hydrogen peroxide hybrid system, SWNTs and hydrogen peroxide form a charge transfer complex accompanied with the suppression of SWNT characteristic NIR absorption or fluorescence spectral intensity. When an antioxidant such as vitamin C is added, the complex immediately reacts with it, with a recovery of the suppressed spectral intensity. The amount of recovered spectral intensity is dependent on the vitamin C concentration.

Limits of detection (LOD) as low as 7 nM can be achieved by this method. The method is therefore far more sensitive than the HPLC method and the electrochemical methods, the former with an LOD of 0.284 µM [5] and the latter with an LOD of 0.276 µM (50 µg/L) [7]. When hydrogen peroxide is in an excess amount, the remaining peroxide continues reacting with SWNTs, so the vitamin C-recovered SWNT spectral intensity decreases again over time. This process is competing with antioxidants possibly remaining in the sample so the decay process may be altered. The decay rate of the spectral intensity or the area of the decay curve is a measure to the total antioxidant concentration in the sample and therefore provides a powerful means to compare the antioxidant capacity of foods, such as various fruit juices, or antioxidant concentration in saliva and blood.

Near infrared absorption can be measured using known instrumentation for use in near-IR spectroscopy. This instrumentation includes a source, a detector, and a dispersive element such as a prism or a diffraction grating to allow the intensity at different wavelengths to be recorded. Fourier transform NIR instruments using an interferometer can also be used. Depending on the sample, the spectrum can be measured in either reflection or transmission.

Any source emitting near infrared radiation can be used. Non limiting examples of broadband sources of near infrared radiation for analytical applications include incandescent lamps and quartz halogen light bulbs. Light-emitting diodes (LEDs) and laser diodes can also be used as can other known sources of near-IR radiation.

The type of detector is also not limited. Suitable detectors include, but are not limited to, silicon-based CCDs, InGaAs and PbS devices.

The assay method described herein has a number of advantages. The SWNTs used in the method are reusable due to the robust structure of SWNTs. The SWNTs are also stable and do not interact with test samples. They can be used with hydrophilic and hydrophobic antioxidants. They can be used for a broad range of samples such as foods or blood. They can be used for in vivo detection. They require a very small amount of sample due to the high sensitivity. The assay can be used to provide versatile measurement variables including optical and electrical variables. Optical variables include near infrared absorption, near infrared fluorescence, and near infrared resonant Raman scattering. Electrical variables include current, voltage and conductivity based on electronic devices such as field effect transistors.

Unique NIR Properties of SWNTs

The NIR features are in an important spectral window (800-1500 nm) that could be covered by the semiconducting laser wavelengths currently used in optical communications. Their spectra fall into the biologically transparent NIR region of 800-1300 nm, making them attractive for in vivo biological optical detection applications. They possess a low NIR absorption background and a high NIR fluorescence contrast, which may allow them to serve as a fluorophore in biochemically targeted tissue markers for selective detection and imaging. They are highly photostable and do not photobleach. Their nano-sized one-dimensional structure may allow them to be integrated into miniature devices with other nanosensors such as field effect transistor sensors. The same material SWNTs alone can also be developed for free radical sensing. Thus SWNTs and their hybrids may offer multi-functionalities for optical biosensing.

The process described herein has been demonstrated using four samples: Vitamin C-fortified water, commercial orange juice, grapefruit juice and vitamin C supplemented apple juice in which the vitamin C concentration is adjusted to the same value. In fruits, other phytochemicals such as carotenoids and flavanones are present so the actual total antioxidant concentration is higher in the fruit juices than in the vitamin C-fortified water. Thus, even with the same amount of vitamin C, the rate of the SWNT spectral intensity decrease is much slower in fruit juices than in vitamin C-fortified water. The results confirm that the SWNT-hydrogen peroxide hybrid system is able to measure the antioxidant capacity in a sample with a standard reference antioxidant such as vitamin C. The system provides a dual sensing capability for detecting antioxidants based on the NIR spectral intensity recovery, or the decay curve (the decay rate and/or the area) of the spectral intensity suppression.

EXPERIMENTAL

The practice of this invention can be further understood by reference to the following examples, which are provided by way of illustration only are not intended to be limiting.

Figure 1:
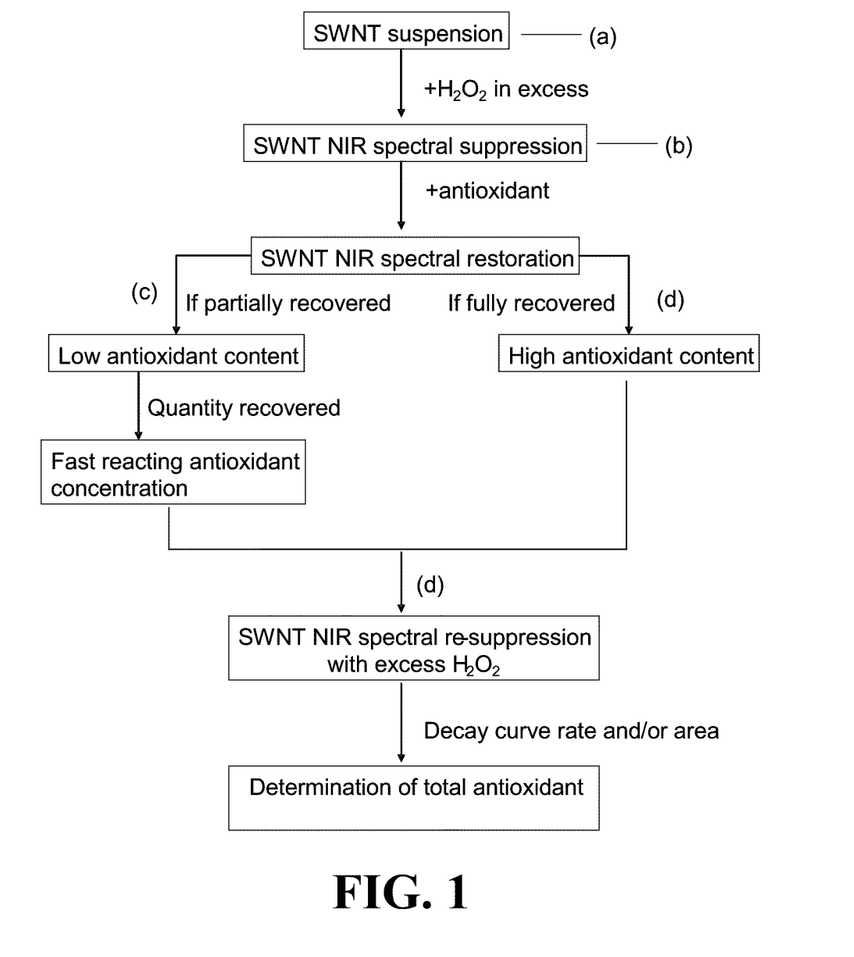
FIG. 1 is a flowchart showing a methodology for determining the total antioxidant capacity of a sample.
Figure 2:
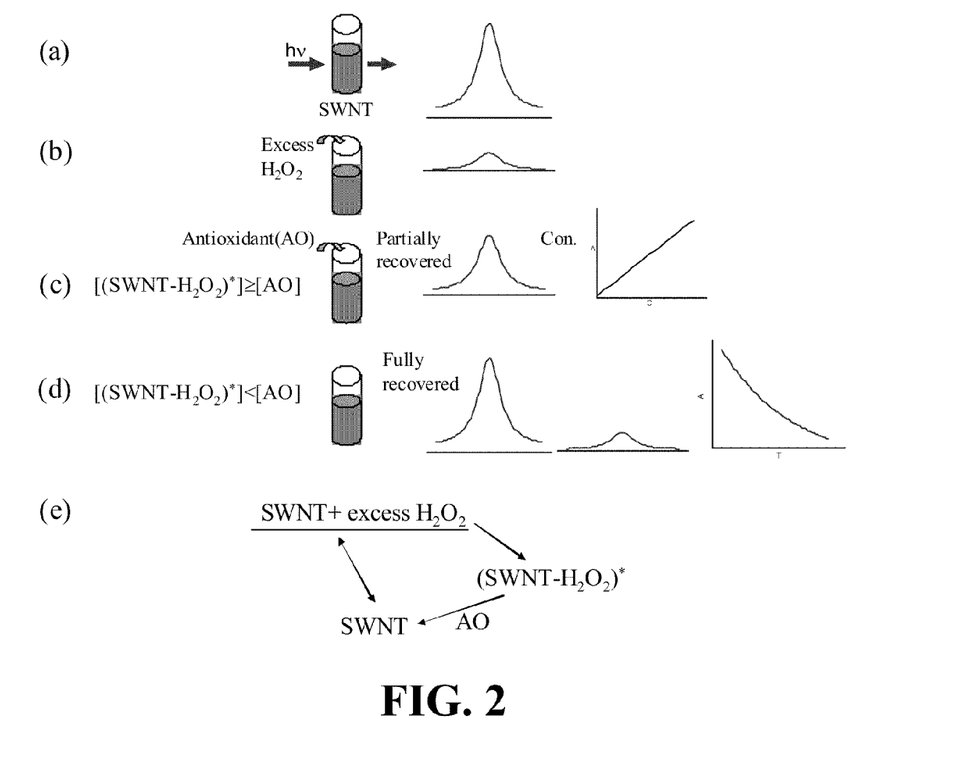

The procedure for antioxidant sensing using an SWNT-hydrogen peroxide hybrid is shown in FIGS. 1 and 2. All experiments were conducted at room temperature.

Example 1

SWNT Suspension Preparation

Figure 3:
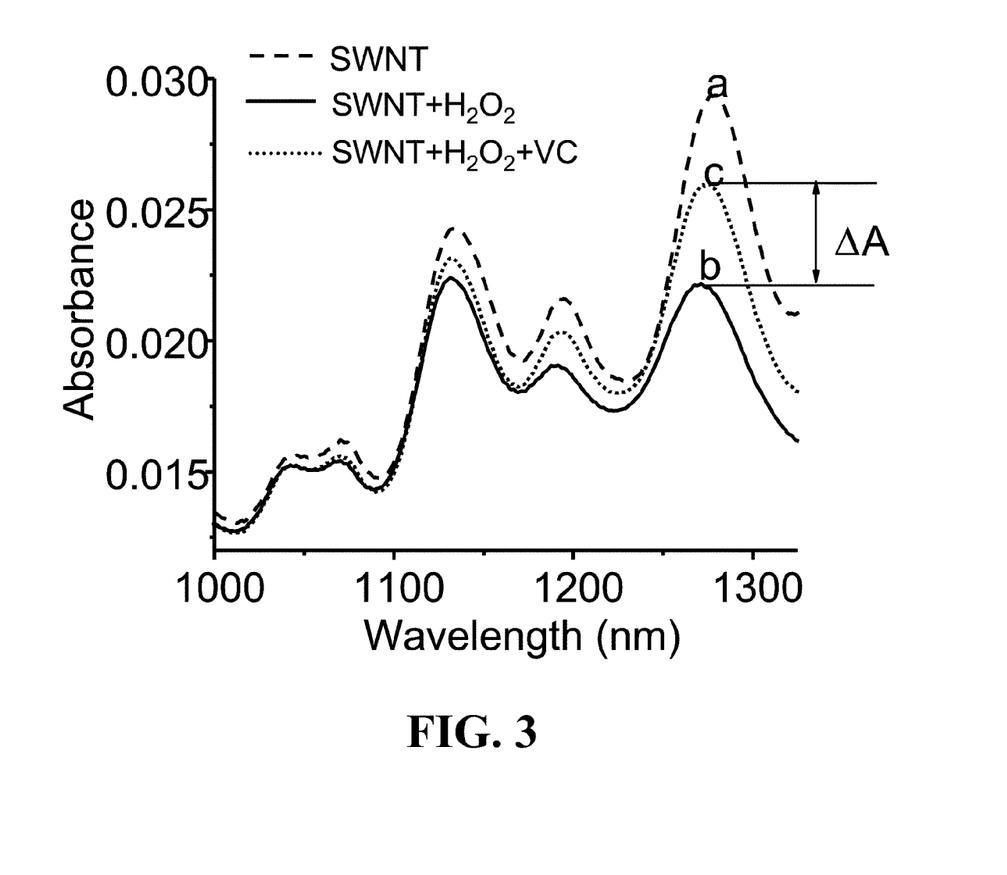
FIG. 3 is a graph showing (a) the near infrared absorption spectra of a SWNT suspension, (b) an SWNT-hydrogen peroxide hybrid suspension, and (c) the SWNT-hydrogen peroxide hybrid suspension in (b) after addition of vitamin C, wherein ΔA is the absorbance change induced by the addition of vitamin C (VC).

In a typical experiment, 1.0 mg of pristine HiPco SWNTs and 1.0 mg of single-stranded (ss) DNA $(GT)_{40}$ [16] or double-stranded (ds) DNA [17] are weighed on a microgram-scaled balance and mixed in a 1.5 mL Eppendorf Flex-Tube with 1.0 ml of a pH 7.0 buffer such as 2-(4-morpholino)ethanesulfonic acid (MES) and tris(hydroxymethyl)-aminomethane (Tris). Other surfactants such as sodium dodecyl sulfate (SDS) (1 wt %) can also be used [18]. The sample is ultrasonicated in an ice-water bath for 1 hour (Sonics model VCX 130 PB, 20 kHz, output power ~8 W) to disperse the nanotubes. The sample is then centrifuged at 16,000 g (VWR Galaxy 16 Microcentrifuge) for 4-18 hours. The supernatant is extracted and diluted with the buffer so that the absorbance at 1270 nm was 0.03 (1 mm pathlength, ~10 μg SWNT/mL) for the experiments. The peak at 1270 nm could be assigned to the first interband transition of (10,5) carbon nanotubes [16], which are more sensitive to environment changes [16-20]. 0.3 ml of the suspension is transferred into a 1 mm pathlength quartz cell and the UV-NIR absorption spectrum is measured on a Varian Cary 5000 UV-Vis-NIR spectrophotometer with the buffer as a background. The spectrum references as a fully recovered spectrum (FIG. 3, plot a).

Example 2

SWNT-Hydrogen Peroxide Hybrid Preparation $H_2O_2$ solution (1.5 wt %) in calculated volumes is added to a ~300 μL ssDNA-SWNT suspension. The final concentration of $H_2O_2$ in the sample is ~200 ppm, usually in an excess amount. The mixture stays overnight and ready for use. The mixture hybrid is transferred into a 1 mm pathlength quartz cell and the UV-NIR absorption spectrum is measured with the buffer as a background. The spectrum references as a fully suppressed spectrum (FIG. 3, plot b). The minimum hybrid sample volume, ~0.3 mL, containing ~3 μg SWNT, is limited by the relatively large light beam size used in the spectrophotometer. The volume can be further reduced to a few microliter in a smaller sample holder when a smaller light beam is used, for example, a NIR semiconductor laser diode. Thus only nanograms of SWNTs may be needed for the measurement, offering a low cost sensing method.

Example 3

Measurement of Antioxidant Samples Using Vitamin C

Fresh vitamin C solutions are prepared in freshly boiled distilled water. For fruit samples and plasma samples, filtration using filtration membranes and/or applying centrifuging are performed to remove large molecules or insoluble components. Three fruit juices, Mott's® Apple Juice, Simply Grapefruit® (100% grapefruit juice) and Simply Orange® (100% orange juice) are used here. The vitamin C concentration in fruit juices is pre-determined by traditional iodometric titration method as a control [2]. For SWNT hybrid optical sensing method, ~1-50 μL of samples containing vitamin C are added into the hybrids in 1 mm pathlength quartz cells. Time-dependent UV-NIR absorption spectra are measured. The buffer solution without HiPco nanotubes is used as a reference for background subtraction. The recovered spectrum after addition of the antioxidant sample is measured (FIG. 3, plot c) and the recovered absorbance ΔA is determined (FIG. 3). The quick recovery result suggests a fast response time and may be related to vitamin C which reacts with $H_2O_2$ much faster.

Example 4

Standard Curve and Detection Limit

Figure 4:
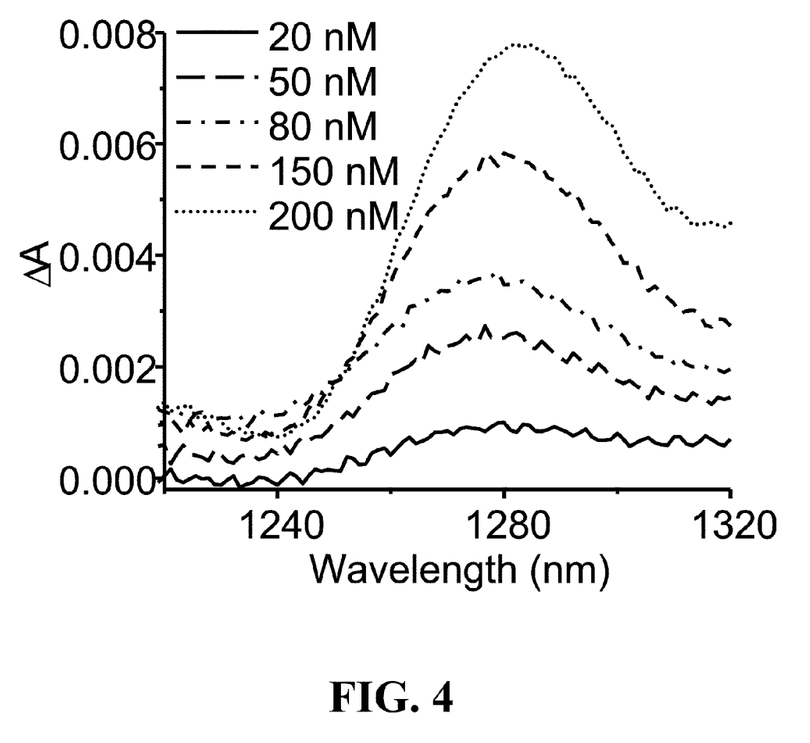
FIG. 4 is a graph showing the concentration-dependent difference spectra (absorbance ΔA) of SWNT-hydrogen peroxide hybrids at different vitamin C concentrations.
Figure 5:
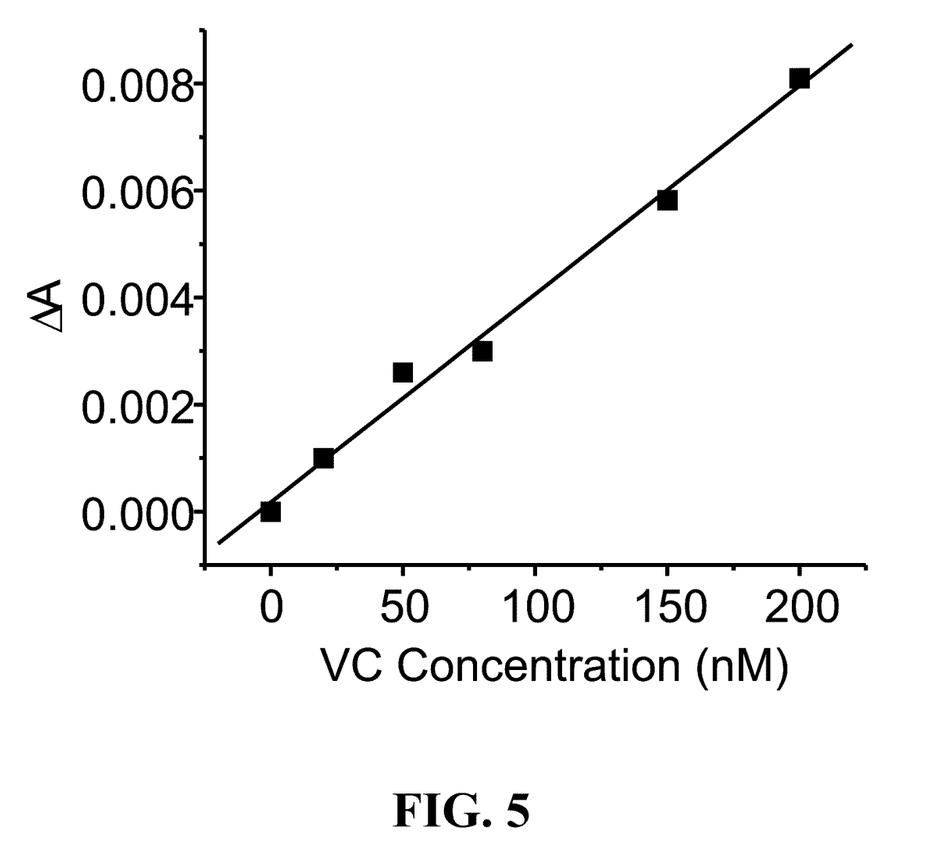
FIG. 5 is a graph showing the induced absorbance change ΔA of SWNT-hydrogen peroxide hybrids at 1270 nm vs. vitamin C concentrations.

The difference spectra of SWNT-hydrogen peroxide hybrids are measured at different vitamin C concentration (FIG. 4), where the fully suppressed spectra serve as a reference. A linear response range is found between 0 and 200 nM, above which ΔA saturation is observed. A standard curve is plotted using ΔA as a function of different vitamin C concentrations (FIG. 5). A linear fit results a linear relationship $\Delta A = 4.015 \times 10^{-5}$ [C], where [C] is the concentration of vitamin C in nM. The limit of detection (LOD), defined as the concentration at which the magnitude of the spectral intensity change is three times larger than the instrumental noise (~0.0001), is determined. The LOD is 7 nM for the 1270 nm band.

Using the standard curve, the vitamin C concentration in an unknown sample containing vitamin C can be determined. If the identity of the antioxidants in an unknown sample is not known, the antioxidant concentration in the sample is determined as a quantity in vitamin C. Since the method is ultra-sensitive to vitamin C in a nanomolar concentration range, only extremely small sample volume is required for analysis. For higher concentration samples, dilution and/or reducing sample volume may be needed to ensure that the concentration to be measured is in the standard curve concentration range.

Since the representative reactive oxidative agent $H_2O_2$ is used here with high sensitivity, the current sensing method may also offer the capability to measure an antioxidant's ability to prevent the formation of oxidants under conditions similar to living organisms.

Example 5

Decay Rates and Decay Curves for Total Antioxidant Capacity

Figure 6:
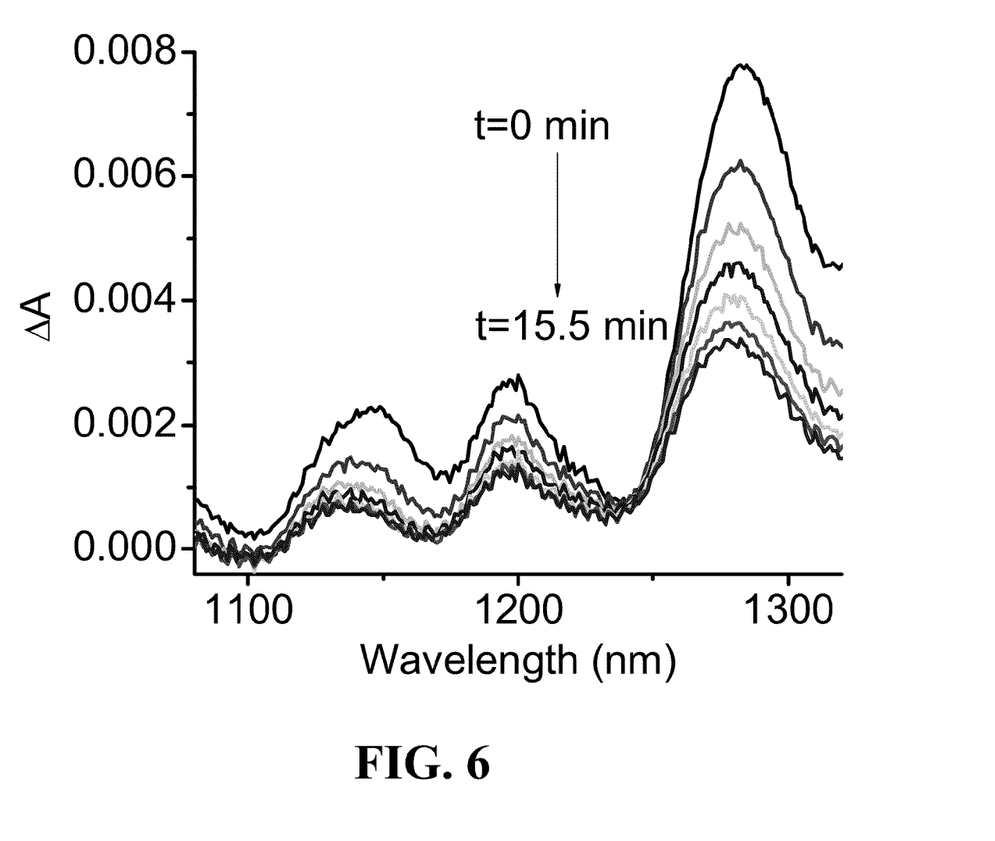
FIG. 6 is a graph showing the time-dependent difference spectra (absorbance ΔA) of a SWNT-$H_2O_2$ hybrid after addition of 200 nM vitamin C.
Figure 7:
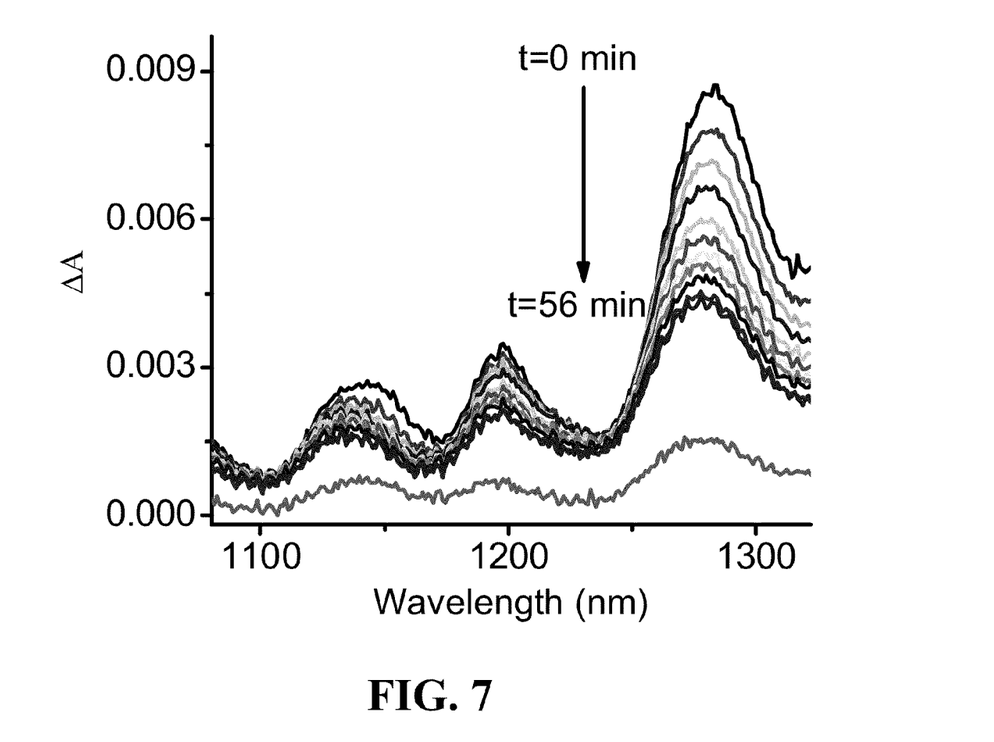
FIG. 7 is a graph showing the time-dependent difference spectra (absorbance ΔA) of a SWNT-$H_2O_2$ hybrid after addition of grapefruit juice containing 200 nM vitamin C.
Figure 8A:
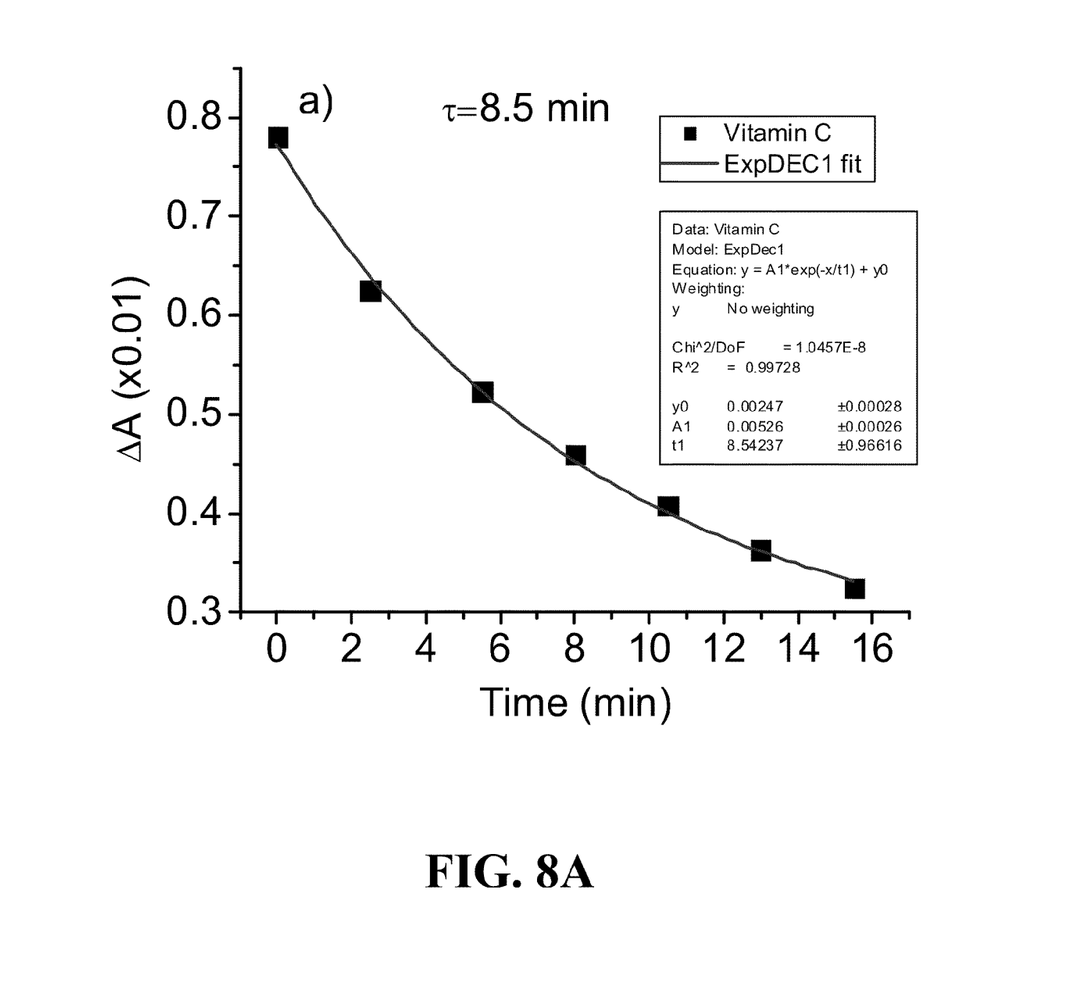
FIG. 8A is a graph showing the time-dependent absorbance change (ΔA) of SWNT-$H_2O_2$ hybrids at 1270 nm changes as a function of reaction time upon addition of 200 nM vitamin C wherein the solid lines are the single exponential fits.
Figure 8B:
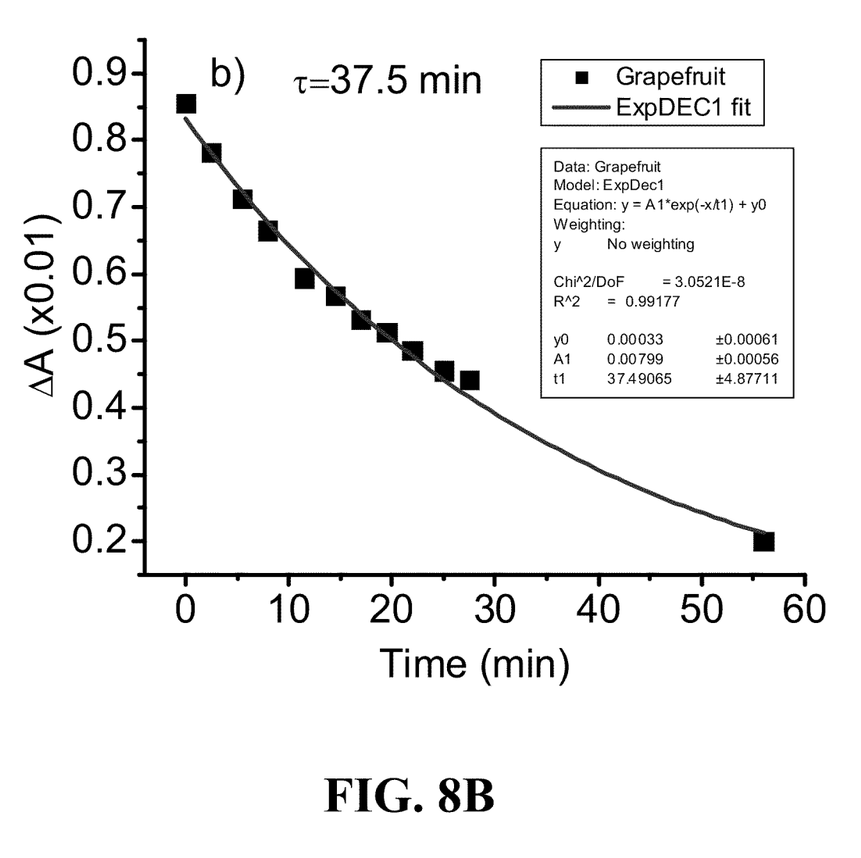
FIG. 8B is a graph showing the time-dependent absorbance change (ΔA) of SWNT-$H_2O_2$ hybrids at 1270 nm changes as a function of reaction time upon addition of grapefruit juice containing 200 nM vitamin C wherein the solid lines are the single exponential fits.

After the spectral intensity recovers to its maxima, it starts to decay again due the reaction of SWNTs with excess $H_2O_2$ (FIG. 6). If there exists an excess amount of vitamin C or other antioxidants, these antioxidants may compete with SWNTs to react with $H_2O_2$, so the spectral intensity decay (FIG. 7) may be slower than the sample containing only vitamin C (FIG. 6). The decay rate ratio or the decay curve area ratio of the sample to a vitamin C standard (FIG. 8) can be used to give a relative quantity of total antioxidant capacity in the sample.

Example 6

Reversibility and Reusability

Figure 9:
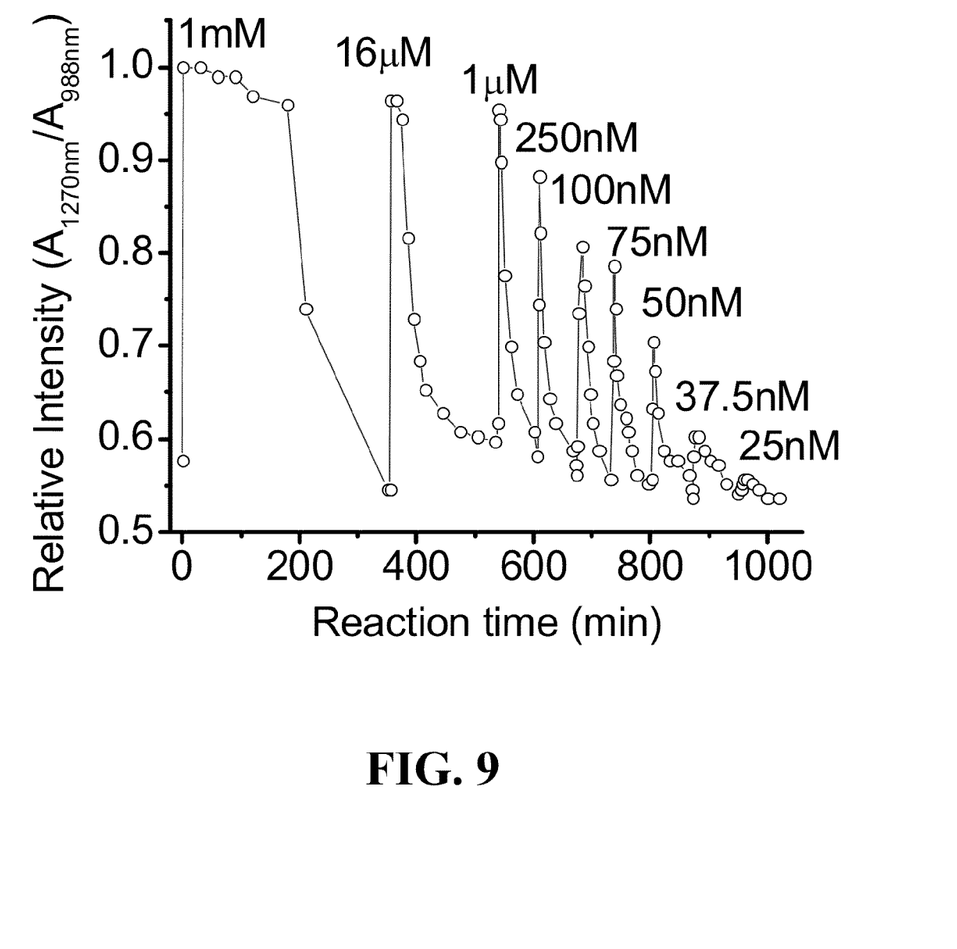
FIG. 9 is a graph showing the induced absorbance change at 1270 nm plotted as $A_{1270\ nm}/A_{988\ nm}$ for SWNT-hydrogen peroxide hybrids at different vitamin C concentrations, showing the reversibility and reusability of the hybrids.

In addition to the extremely high sensitivity, the current method also offers reversibility and reusability. As demonstrated in FIG. 9, the hybrids respond to different does of vitamin C reversibly, which can be related to the robust structure of SWNTs [10-20], which is not damaged by $H_2O_2$ [16-20].

While the foregoing specification teaches the principles of the present invention, with examples provided for the purpose of illustration, it will be appreciated by one skilled in the art from reading this disclosure that various changes in form and detail can be made without departing from the true scope of the invention.

REFERENCES

[1] L. Pauling, Vitamin C and the Common Cold, San Francisco, Calif., W. H. Freeman and Company, 1970.
[2] Collins, C. H.; Silva, C. R.; Simoni, J. A.; Volpe, P. L. O. J. Chem. Educ., 1999, 76, 1421-1422. Ascorbic acid as a Standard for Iodometric Titrations.
[3] Paim, A. P.; Reis, B. F. Anal. Sci., 2000, 16, 487-491. An Automatic Spectrophotometric Titration Procedure for Ascorbic Acid Determination in Fruit Juices and Soft Drinks Based on Volumetric Fraction Variation.
[4] A. Zafra-Gomez, A. Garballo, J. C. Morales, L. E. Garcia-Ayuso, J. Agric. Food Chem. 54 (2006) 4531-4536. Simultaneous Determination of Eight Water-Soluble Vitamins in Supplemented Foods by Liquid Chromatography.
[5] A. M. Maia, A. R. Baby, W. J. Yasaka, E. Suenaga, T. M. Kaneko, M. V. R. Velasco, Talanta 71 (2007) 639-643. Validation of HPLC Stability-indicating Method for Vitamin C in Semisolid Pharmaceutical/Cosmetic Preparations with Glutathione and Sodium Metabisulfite, as Antioxidants.
[6] Lagier, C. M.; Verdini, R. A. J. Agric. Food Chem., 2000, 48, 2812-2817. Voltammetric Iodometric Titration of Ascorbic Acid with Dead-Stop End-Point Detection in Fresh Vegetables and Fruit Samples.
[7] T. Rohani, M. A. Taher, Talanta 78 (2009) 743-747. A New Method for Electrocatalytic Oxidation of Ascorbic Acid at the Cu(II) Zeolite-Modified Electrode.
[8] X. Wu, L. Gu, J. Holden, D. B. Haytowitz, S. E. Gebhardt, G. Beecher, R. L. Prior, J. Food Compo. Anal. 17 (2004) 407-422. Development of A Database for Total Antioxidant Capacity in Foods: A Preliminary Study.
[9] D. Huang, B. Ou, R. L. Prior, J. Agric. Food Chem. 53 (2005) 1841-1856. The Chemistry behind Antioxidant Capacity Assays.
[10] Ph. Avouris, Z. Chen, V. Perebeinos, Nature Nanotech. 2 (2007) 605-615. Carbon-Based Electronics.
[11] L. Zhang, S. Zaric, X. Tu, W. Zhao, H. Dai, J. Am. Chem. Soc. 130(8) (2008) 2686-2691 Assessment of Chemically Separated Carbon Nanotubes for Nanoelectronics.
[12] D. A. Tsyboulski, S. M. Bachilo, R. B. Weisman, Nano Lett. 5 (2005) 975-979. Versatile Visualization of Individual Single-Walled Carbon Nanotubes with Near-Infrared Fluorescence Microscopy.
[13] P. Cherukuri, S. M. Bachilo, S. H. Litovsky, R. B. Weisman, J. Am. Chem. Soc. 126 (2004) 15638-15639. Near-Infrared Fluorescence Microscopy of Single-Walled Carbon Nanotubes in Phagocytic Cells.
[14] W. Zhao, C. Song, P. E. Pehrsson, J. Am. Chem. Soc. 124 (2002) 12418-12419. Water-Soluble and Optically pH Sensitive Single-Walled Carbon Nanotubes from Surface Modification.
[15] Z. Liu, C. Davis, W. Cai, L. He, X. Chen, H. Dai., PNAS 105 (2008) 1410-1415. Circulation and Long-Term Fate of Functionalized, Biocompatible Single-Walled Carbon Nanotubes in Mice Probed By Raman Spectroscopy
[16] X. Tu, P. E. Pehrsson, W. Zhao, J. Phys. Chem. C. 111 (2007) 17227-17231. Redox Reaction of DNA-Encased HiPco Carbon Nanotubes with Hydrogen Peroxide: A Near Infrared Optical Sensitivity and Kinetics Study.
[17] Y. Xu, P. E. Pehrsson, L. Chen, R. Zhang, W. Zhao, J. Phys. Chem. C. 111 (2007) 8638-8643. Double Stranded DNA-Single Walled Carbon Nanotube Hybrids for Optical Hydrogen Peroxide and Glucose Sensing.
[18] C. Song, P. E. Pehrsson, W. Zhao, J. Phys. Chem. B. 109 (2005) 21634-21639. Recoverable Solution Reaction of HiPco Carbon Nanotubes with Hydrogen Peroxide.
[19] C. Song, P. E. Pehrsson, W. Zhao, J. Mater. Res. 21 (2006) 2817-2823. Optical Enzymatic Detection of Glucose Based on Hydrogen Peroxide-Sensitive HiPco Carbon Nanotubes.
[20] Y. Xu, P. E. Pehrsson, L. Chen, W. Zhao, J. Am. Chem. Soc, 130(31) (2008) 10054-10055. Controllable Redox Reaction of Chemically Purified DNA-Single Walled Carbon Nanotube Hybrids with Hydrogen Peroxide.

What is claimed is:

1. A method comprising:
 measuring a first absorbance value of a composition comprising a charge transfer complex of single walled carbon nanotubes and $H_2O_2$ at one or more wavelengths in the near infra-red;
 adding a sample to the composition;
 subsequently measuring a second absorbance value of the composition at the one or more wavelengths; and
 determining the difference between the first and second absorbance values;
 wherein the difference between the first and second absorbance values is an indication of the antioxidant concentration or the antioxidant capacity of the sample;
 wherein the composition comprises $H_2O_2$ in excess such that some of the $H_2O_2$ molecules are part of the charge transfer complex and some of the $H_2O_2$ molecules are not part of the charge transfer complex prior to adding the sample to the composition.

2. The method of claim 1, further comprising:
 measuring one or more additional absorbance values of the composition at the one or more wavelengths, wherein the second absorbance value and the one or more additional absorbance values are each measured at a different time after adding the sample to the composition;
 determining the difference between each of the one or more additional absorbance values and the first absorbance value; and
 determining the rate of change of the difference in absorbance value or the area under a curve of the difference in absorbance value as a function of time.

3. The method of claim 2, further comprising:
 determining the rate of change of the difference in absorbance value or the area under a curve of the difference in absorbance value as a function of time for a second sample different than the sample; and
 comparing the rate of change or the area under the curve of the two samples;
 wherein the difference in the rate of change or the difference in the area under the curve between the two samples is an indication of the different antioxidant capacities of the samples.

4. The method of claim 3, wherein the sample and the second sample are each food samples.

5. The method of claim 3, wherein the sample and the second sample are each a fruit juice.

6. The method of claim 3, wherein the second sample is a vitamin C standard and wherein the difference in the rate of change or the difference in the area under the curve between the sample and the vitamin C standard is an indication of the relative quantity of total antioxidant capacity in the sample.

7. The method of claim 1, wherein:
 measuring the first and second absorbance values comprises measuring absorbance across a spectrum of wavelengths in the near infra-red; and
 wherein determining the difference between the first and second absorbance values comprises determining the difference between: 1) the area under a curve of the first absorbance value as a function of wavelength; and 2) the area under a curve of the second absorbance value as a function of wavelength.

8. The method of claim 7, further comprising:
 measuring one or more additional absorbance values of the composition across a spectrum of wavelengths, wherein the second absorbance value and each of the one or more additional absorbance values are measured at a different time after adding the sample to the composition;
 determining the difference between: 1) the area under a curve of the first absorbance value as a function of wavelength; and 2) the area under a curve of each of the one or more additional absorbance values as a function of wavelength; and
 determining the rate of change of the difference in absorbance value or the area under a curve of the difference in absorbance value as a function of time.

9. The method of claim 1, wherein the antioxidant comprises Vitamin C.

10. The method of claim 1, wherein each of the first and second absorbance values are measured at one or more wavelengths between 600 nm and 2500 nm.

11. The method of claim 10, wherein each of the first and second absorbance values are measured at one or more wavelengths between 1000 nm and 1400 nm.

12. The method of claim 10, wherein each of the first and second absorbance values are measured at one or more wavelengths between 1220 nm and 1320 nm.

13. The method of claim 10, wherein each of the first and second absorbance values are measured at one or more wavelengths between 1260 nm and 1300 nm.

14. The method of claim 1, wherein the sample comprises blood or saliva.

15. The method of claim 1, wherein the sample is a food sample.

16. The method of claim 1, wherein the sample is a fruit juice.

17. The method of claim 1, further comprising determining the antioxidant concentration in the sample from the difference between the first and second absorbance values.

18. The method of claim 1, wherein adding the sample to the composition results in an initial increase in absorbance of the composition followed by a decrease in absorbance and wherein the method further comprises:
 measuring the rate of decrease of the absorbance during the decrease in absorbance; or
 measuring the area under a decay curve of the difference in absorbance value as a function of time during the decrease in absorbance.

19. A method comprising:
 (a) measuring a first absorbance value of a composition comprising a charge transfer complex of single walled carbon nanotubes and $H_2O_2$ at one or more wavelengths in the near infra-red;
 (b) adding a calibration sample comprising a known concentration of an antioxidant to the composition;
 (c) subsequently measuring a second absorbance value of the composition at the one or more wavelengths;
 (d) determining the difference between the first and second absorbance values;
 (e) repeating steps (a)-(d) for one or more additional calibration samples having different known concentrations of the antioxidant; and
 (f) determining the relationship between antioxidant concentration and the difference between the first and second absorbance values;
 wherein the composition comprises $H_2O_2$ in excess such that some of the $H_2O_2$ molecules are part of the charge transfer complex and some of the $H_2O_2$ molecules are not part of the charge transfer complex prior to adding the sample to the composition.

20. The method of claim 19, wherein determining the relationship between antioxidant concentration and the difference between the first and second absorbance values comprises generating a linear fit to a plot of the difference between the first and second absorbance values as a function of antioxidant concentration.

21. The method of claim 19, further comprising:
measuring an absorbance value of the composition comprising single walled carbon nanotubes and $H_2O_2$ at the one or more wavelengths in the near infra-red;
adding a test sample comprising an unknown concentration of one or more antioxidants to the composition;
measuring the absorbance value of the composition at the one or more wavelengths after adding the test sample;
determining the difference between the absorbance value of the composition after adding the test sample and the absorbance value before adding the test sample; and
using the relationship between antioxidant concentration and the difference between the first and second absorbance values to determine the antioxidant concentration of the test sample.

22. The method of claim 21, wherein the test sample comprises Vitamin C.

23. The method of claim 21, wherein the test sample comprises at least two different antioxidants.

24. The method of claim 21, wherein the test sample is a fruit juice.

25. The method of claim 19, wherein the antioxidant in the calibration samples is Vitamin C.

* * * * *